(12) United States Patent
Evans et al.

(10) Patent No.: US 7,297,402 B2
(45) Date of Patent: Nov. 20, 2007

(54) SHAPED PARTICLE HAVING AN ASYMMETRICAL CROSS SECTIONAL GEOMETRY

(75) Inventors: Corey Ryan Evans, Houston, TX (US); James Allen Wambaugh, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/077,471

(22) Filed: Mar. 10, 2005

(65) Prior Publication Data

US 2005/0232853 A1    Oct. 20, 2005

Related U.S. Application Data

(60) Provisional application No. 60/562,581, filed on Apr. 15, 2004.

(51) Int. Cl.
*B32B 5/16* (2006.01)
*B01J 23/74* (2006.01)

(52) U.S. Cl. .................................. 428/402; 428/543

(58) Field of Classification Search ................ 428/402, 428/543
See application file for complete search history.

(56) References Cited

U.S. PATENT DOCUMENTS

| | | | |
|---|---|---|---|
| 3,232,887 A | 2/1966 | Pessimisis et al. | 252/435 |
| 3,966,644 A | 6/1976 | Gustafson | 252/455 |
| 4,342,643 A * | 8/1982 | Kyan | 208/134 |
| 4,391,740 A | 7/1983 | Gibson | 252/470 |
| 4,495,307 A | 1/1985 | Clements | 502/305 |
| 4,673,664 A | 6/1987 | Bambrick | 502/439 |
| 4,758,543 A | 7/1988 | Sherrod et al. | 502/174 |
| 4,804,799 A | 2/1989 | Lewis et al. | 585/444 |
| 5,097,091 A | 3/1992 | Kremer | 585/444 |
| 5,330,958 A * | 7/1994 | Viola et al. | 502/316 |
| 5,376,613 A | 12/1994 | Dellinger et al. | 502/304 |
| 5,689,023 A | 11/1997 | Hamilton, Jr. | 585/444 |
| 6,551,958 B1 | 4/2003 | Baier et al. | 502/304 |
| 6,624,114 B1 * | 9/2003 | Eberle et al. | 502/439 |
| 2003/0144566 A1 | 7/2003 | Culp et al. | 585/444 |

FOREIGN PATENT DOCUMENTS

| | | |
|---|---|---|
| DE | 102 26 729 A1 | 1/2004 |
| EP | 0794004 | 6/2003 |

OTHER PUBLICATIONS

International Search Report for PCT/US2005/012625 of Jun. 22, 2005.
Written Opinion for PCT/US2005/012625 of Jun. 22, 2005.

* cited by examiner

*Primary Examiner*—H. T Le

(57) ABSTRACT

A shaped particle suitable for use as a catalyst support or, alternatively, a dehydrogenation catalyst system in the form of a shaped particle, wherein said shaped particle has a geometry including a length and a cross sectional geometry at at least one point along said length, wherein said cross sectional geometry is defined by an asymmetrical shape having an imaginary dividing line providing for an upper end, having an upper end cross sectional area, and a lower end, having a lower end cross sectional area, wherein said upper end cross sectional area is greater than said lower end cross sectional area. The cross sectional geometry may further be characterized as having a perimeter and as defining a plurality of notches with each said notch of said plurality of notches having a groove depth and a groove opening rotational distance.

7 Claims, 2 Drawing Sheets

US 7,297,402 B2

SHAPED PARTICLE HAVING AN ASYMMETRICAL CROSS SECTIONAL GEOMETRY

This application claims the benefit of U.S. Provisional Application Ser. No. 60/562,581, filed Apr. 15, 2004.

The invention relates to a shaped particle. In one aspect, the invention relates to a shaped particle that can suitably be used as a catalyst support. Another aspect of the invention relates to a shaped particle catalyst system having a specific geometry.

There has been an ongoing effort to design and develop shaped catalyst particles that provide for certain desired properties or even improved properties over certain prior art shapes when used in a reactor catalyst bed of a catalytic process. A number of catalyst shapes have been described in the prior art.

U.S. Pat. No. 3,966,644 discloses a shaped porous hydrotreating catalyst particle characterized by having a cross section with a concave geometry, which extends for a sufficient length along its axis so as to provide a solid particle. The concave geometry is preferably polylobal in that the lobes arise from circles of equal diameter and are connected so as to form a closed curve. The more preferred cross sectional geometry of the particle is a polylobal shape with three or more lobes of circles of equal diameter. The taught concaved shaped hydrotreating catalyst is presented as having advantageous catalytic activity in the hydrotreatment of petroleum residue. It is significant to note that the shapes taught by the '644 patent are either radially symmetrical or bilaterally symmetrical.

U.S. Pat. No. 4,391,740 discloses a shaped extruded catalyst particle having a polylobal cross-section that may be used in the hydroprocessing of hydrocarbon feedstocks containing sulfur and metals. The catalyst particles may be elongated extrudates of a defined non-circular cross-section that can be circumscribed by a rectangle of particular dimensions. Specific shapes include an oval cross-section, or an oval with a bump cross-section, or an oval with two bumps cross-section. It is asserted that the shapes of the '740 patent provide for an improved surface-to-volume ratio of the particle and that beds of the shaped catalyst will give lower pressure drops than other comparative shapes. It is noted that the shapes taught by the '740 patent are symmetrical.

U.S. Pat. No. 4,495,307 discloses a cylindric hydrotreatment catalyst particle having a polylobate cross-section in which the individual lobes are separated by concave interstices that are bluntly rounded with greater curvature than that of the lobes. The shape may further be defined with reference to an equilateral triangle. The taught shaped catalyst of the '307 patent is purported to have improved properties over the prior art trilobe shaped catalyst particles as are described in U.S. Pat. No. 3,232,887 such as providing for better catalytic activity and improvement in pressure drop. It is noted that the shapes taught by the '307 patent are bilaterally symmetrical.

U.S. Pat. No. 4,673,664 discloses a hydrotreating catalyst particle, which is helical lobed, polylobal extrudates having the shape of three or four strands wound helically about the axis of extrusion along the length of the particles. The helical shape is supposed to provide for improved pressure drop across a fixed reactor bed of the catalyst particles. It is noted that the shapes taught by the '664 patent are either radially symmetrical or bilaterally symmetrical.

U.S. Pat. No. 5,097,091 discloses toothed-wheel shaped catalyst for use in dehydrogenation of hydrocarbons. The toothed-wheel shaped particles have at least three teeth and specifically defined dimensional ratios for such dimensions as the ratio of crown circle diameter-to-root circle diameter, ratio of gap width on the tooth root-to-tooth width on the crown, and gap width on the tooth root. The tooth shaped catalyst is supposed to provide for improved activity and selectivity relative to a comparative catalyst. It is noted that the shapes taught by the '091 patent are either radially symmetrical or bilaterally symmetrical.

While the catalyst shapes described above may provide for various benefits when used in certain catalytic processes, there is always a need to find catalyst shapes that can provide certain specific benefits that other comparative shapes do not provide or a combination of beneficial properties that may provide improvements over prior art catalyst shapes.

It is, thus, an object of this invention to provide a shaped particle that can suitably be used as a support for catalytic components.

It is another object of this invention to provide a shaped catalyst particle that can be used as a component of a catalyst bed of a reactor system.

Therefore, in accordance with the invention, a shaped particle is provided. The shaped particle has a geometry including a length and a cross sectional geometry at at least one point along the length with the cross sectional geometry being defined by an asymmetrical shape having an imaginary dividing line providing for an upper end, having an upper end cross sectional area, and a lower end, having a lower end cross sectional area. The upper end cross sectional area is greater than the lower end cross sectional area. The shaped particle may suitably be used as a support for a catalyst component, or the shaped particle may itself be a catalyst system.

In accordance with another invention, a dehydrogenation process is provided which comprises contacting under dehydrogenation reaction conditions a dehydrogenation feed with an iron oxide based dehydrogenation catalyst system that is in the form of a shaped particle. The shaped particle comprises iron oxide and has a geometry including a length and a cross sectional geometry at at least one point along the length, wherein the cross sectional geometry is defined by an asymmetrical shape having an imaginary dividing line providing for an upper end, having an upper end cross sectional area, and a lower end, having a lower end cross sectional area, wherein the upper end cross sectional area is greater than the lower end cross sectional area.

Figure 1:
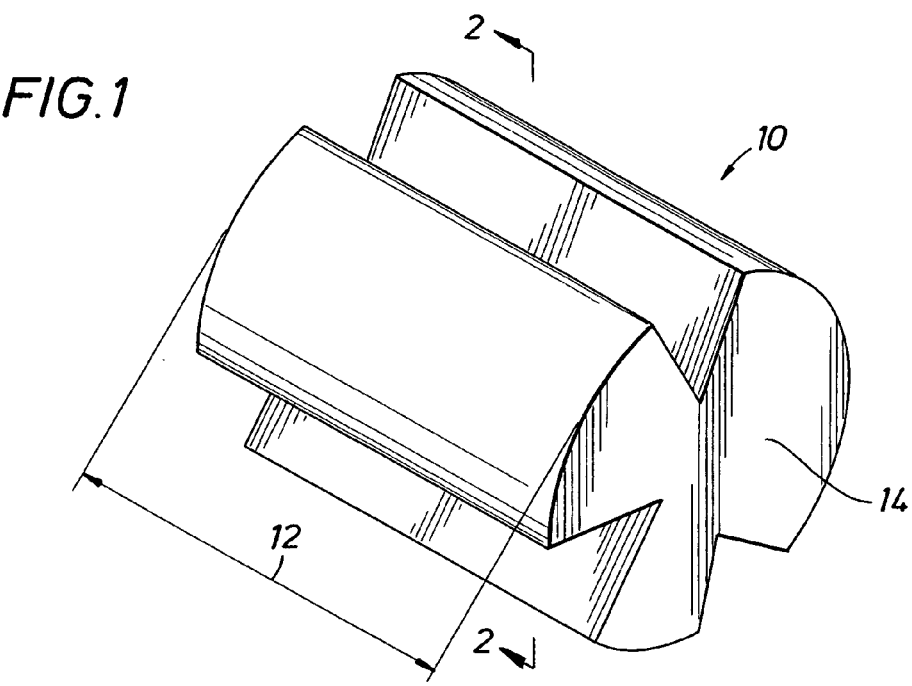
FIG. 1 is a perspective view of a three-grooved embodiment of the inventive shaped particle.

This invention relates to a multi-grooved shaped particle that may suitably be used as a catalyst support onto which a catalytic component is incorporated. A particularly desirable aspect of the invention further relates to a dehydrogenation catalyst system that is in the form of a multi-grooved shaped particle. One unique feature of the multi-grooved shaped particle is in its geometry that provides for a weight-loaded particle. It is believed that the weight loading of the particle promotes a desired orientation and more uniform packing of the multi-grooved shaped particle within a catalyst bed when it is loaded into a reactor to form the catalyst bed. This weight loading of the multi-grooved shaped catalyst particle is particularly important with an iron oxide based multi-grooved shaped catalyst particles that are for use in the dehydrogenation of hydrocarbons.

When referring herein to a weight-loaded particle, what is meant is that the particle has a cross section and a length such that they provide for a shaped particle or pellet having an unsymmetrical cross sectional geometry. The geometry of the cross section of the shaped particle is nonsymmetrical so as to provide a portion of the cross section that has a greater cross sectional area than the remaining portion of the cross section. When the particle having the nonsymmetrical cross section is composed of a homogeneous support material or a homogeneous catalytic material, it will be loaded in the sense that the portion of the particle having the greater cross sectional area will be heavier than the remaining portion due to it containing a greater amount of mass.

An alternative way of characterizing the cross section of the weight-loaded particle is to define the cross section as having at least one imaginary dividing line that passes through a central axis of the weight loaded particle thereby defining two portions of the cross section of the weight loaded particle with a portion of the cross section being on one side of the imaginary dividing line and a remaining portion of the cross section being on the opposite side of the dividing line. When the cross section is defined in this manner, it is preferred for there to be at least one imaginary dividing line that divides the cross section so as to provide a ratio of the cross sectional area of the portion of the cross section to the cross sectional area of the remaining portion of the cross section to be in the range of from about 1.1:1 to about 4:1. A preferred ratio of the cross sectional area of the portion of the cross section to the cross sectional area of the remaining portion of the cross section is in the range of from 1.25:1 to 3:1, and, most preferred, the ratio is in the range of from 1.5:1 to 2.5:1. A typical target for the ratio is about 2:1.

One method of loading a reactor vessel with catalyst particles is to dump them into the reactor vessel and allowing the particles to freely drop into the reactor vessel to form a catalyst bed. Another method may include the use of a loading sock into which the catalyst particles are poured with the sock being used to direct the flow of the catalyst particles within the reactor vessel and to limit the distance that the catalyst particles freely fall before landing upon the catalyst bed being formed. Other methods of loading a reactor vessel may include the use of pneumatic devices or other conveyance devices to transfer the catalyst particles into the reactor vessel. In all of these methods, the catalyst particles that are placed into the reactor vessel fall some distance before landing and forming the catalyst bed within the reactor vessel.

It is believed that the herein described inventive shaped particle will provide for an improved packed catalyst bed by giving a more uniform placement of the shaped particles within the packed bed. Thus, when loaded into a reactor vessel the freely falling, weight loaded particles will orient themselves in such a way in the formed catalyst bed that there is a certain uniformity of the placement of the catalyst particles.

When referring herein to the shaped particle as being nonsymmetrical, what is meant is that the particle lacks both bilateral symmetry and radial symmetry. Bilateral symmetry is when the shape may be divided by a plane into two essentially identical halves. Radial symmetry is when the shape is symmetric in respect to an axis such that similar parts are regularly arranged around a central axis.

To more fully illustrate and describe the inventive shaped particle, reference is now made to the figures presenting various embodiments of the invention. FIG. 1 is a perspective view of a three-grooved shaped particle 10. The three-grooved shaped particle is characterized as having a length 12 and a cross sectional geometry 14 that is asymmetrical in shape. At a point along the length 12 of the three-grooved shaped particle 10, a cross sectional plane 2-2 is taken that is perpendicular to the central axis (not shown) of the three grooved shaped particle 10.

Figure 2:
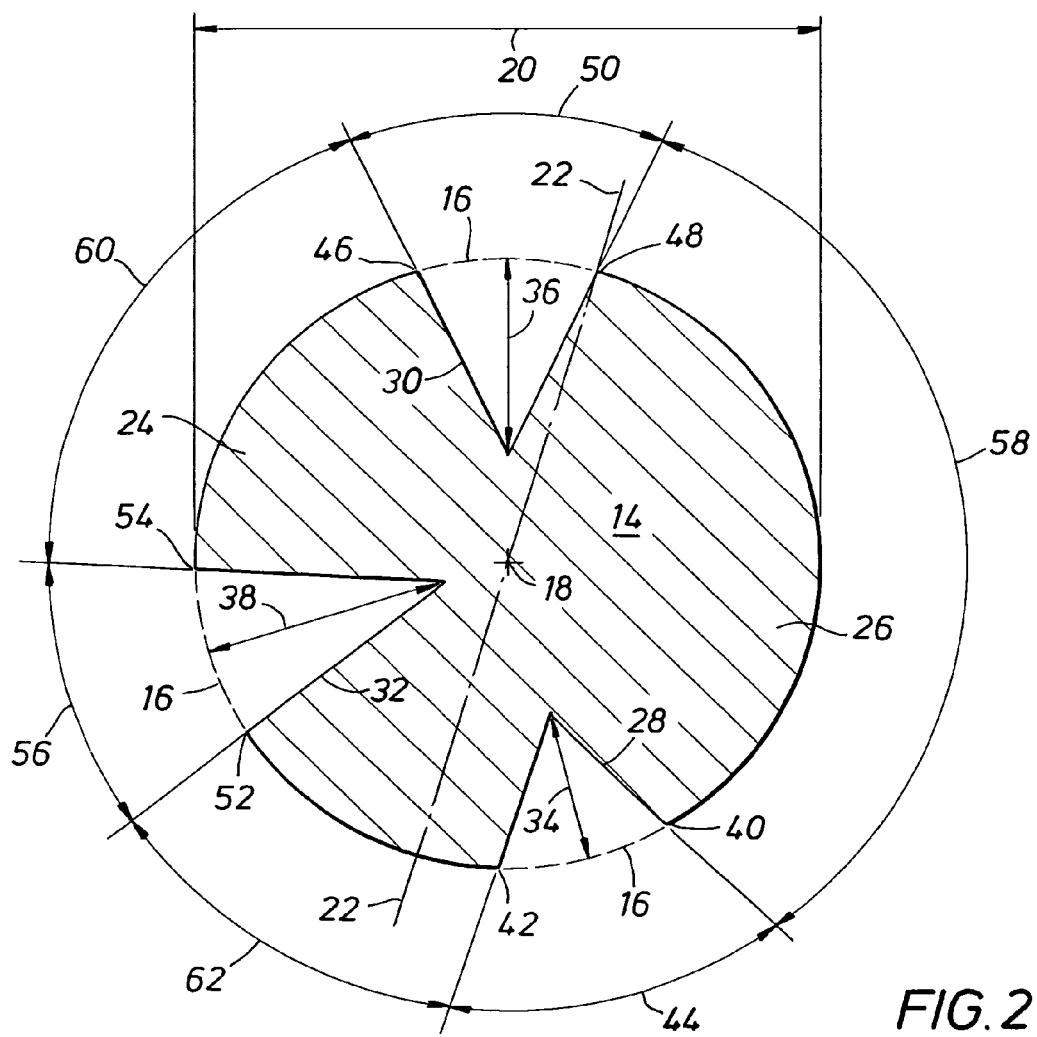
FIG. 2 is a cross sectional view of the three-grooved shaped particle of FIG. 1 taken along section line 2-2.

Referring to FIG. 2, depicted is cross sectional view 2-2 of the cross sectional geometry 14 defined in part by an imaginary perimeter 16, which can have any suitable configuration or shape, but as depicted in FIG. 2, the imaginary perimeter 16 approximates a circle having a central axis 18. The imaginary perimeter 16 is further defined as having a diameter 20 and an imaginary dividing line 22 passing through the axis 18. The imaginary dividing line 22 provides for or otherwise divides the cross sectional geometry 14 into an upper end or half 24 and a lower end or half 26.

The term imaginary perimeter 16, as used herein, refers to the outer boundary or edge of the cross sectional geometry 14, which is generally defined by the die or form by which the three-grooved shaped particle 10 is formed. The imaginary perimeter 16 is imaginary in the sense that, if the cross sectional geometry 14 does not include grooves, the imaginary perimeter 16 would approach a circular shape having a central axis 18. Thus, the central axis 18 is the center of the imaginary perimeter 16. The imaginary dividing line 22 passes through the central axis 18. Again, the imaginary dividing line 22 is imaginary in the sense that, if the cross sectional geometry 14 does not include grooves, the imaginary perimeter 16 would approximate a circular shape. The imaginary dividing line 22 divides the cross sectional geometry 14 into two sections with one of the sections having a greater cross sectional area than the cross sectional area of the other section. Due to the length of the shaped particle, the section having the larger cross sectional area will have a greater mass than the remaining section with the smaller cross sectional area, thus, providing for a loaded shaped particle. It is understood that the imaginary perimeter 16 may generally be circular and that it may be elongated or deviate somewhat from a perfect circle due to variances resulting from manufacturing methods and conditions.

The cross sectional geometry 14 defines a plurality of grooves including first groove 28, second groove 30 and third groove 32. First groove 28, second groove 30 and third groove 32 are respectively defined by a first groove depth 34, second groove depth 36, and third groove depth 38. The groove depth is the shortest distance of a line from a point on the imaginary perimeter 16 to the deepest point of the edge of the groove as measured from the imaginary perimeter 16, wherein the line is perpendicular to the tangent line passing through the point on the imaginary perimeter 16.

The opening of each groove of the plurality of grooves that is defined by the cross sectional geometry 14 can be characterized with reference to the number of degrees of the 360 rotational degrees that defines a circle. Thus, the first groove 28 includes a first leading edge 40 and a first trailing edge 42 that are spaced apart by a first groove opening rotational distance 44, which as previously noted may be measured in terms of degrees. The second groove 30 includes a second leading edge 46 and a second trailing edge 48 that are spaced apart by a second groove opening rotational distance 50. The third groove 32 includes a third leading edge 52 and a third trailing edge 54 that are spaced apart by a third groove opening rotational distance 56.

It is understood that the leading and trailing edges referred to herein are not necessarily well defined points or angles and that the edges may in fact be rounded as a result of use or abrasion or as a result of the manufacturing methods or conditions.

The outer edge of the cross sectional geometry 14 between each of the grooves of the plurality of grooves can be characterized with reference to the number of degrees of the 360 rotational degrees that defines a circle. Thus, the first leading edge 40 of the first groove 28 and the second trailing edge 48 of second groove 30 are spaced apart by a first rotational distance 58. The second leading edge 46 of the second groove 30 and the third trailing edge 54 of the third groove 32 are spaced apart by a second rotational distance 60. The third leading edge 52 of the third groove 32 and the first trailing edge 42 of the first groove 28 are spaced apart by a third rotational distance 62.

In moving along the imaginary perimeter 16 in a counter-clockwise direction, the trailing edge of a groove, for example the first trailing edge 42 of the first groove 28, is first encountered followed by the encountering of the first leading edge of the groove, for example the leading edge 40 of the first groove 28. Next, the second trailing edge 48 of second groove 30 is encountered followed by the encountering of the second leading edge 46 of the second groove 30, and, again, the third trailing edge 54 of the third groove 32 is encountered followed by the encountering of the third leading edge 52 of the third groove 32 and back to the beginning at the first trailing edge 42. The imaginary perimeter 16 starting at a point such as the first trailing edge of the first groove 28 and ending at the same spot represents 360 degrees. Thus, the summation of the first groove opening rotational distance 44, the second groove opening rotational distance 50, the third groove opening rotational distance 56, the first rotational distance 58, the second rotational distance 60, and the third rotational distance 62 is 360 degrees.

Figure 3:
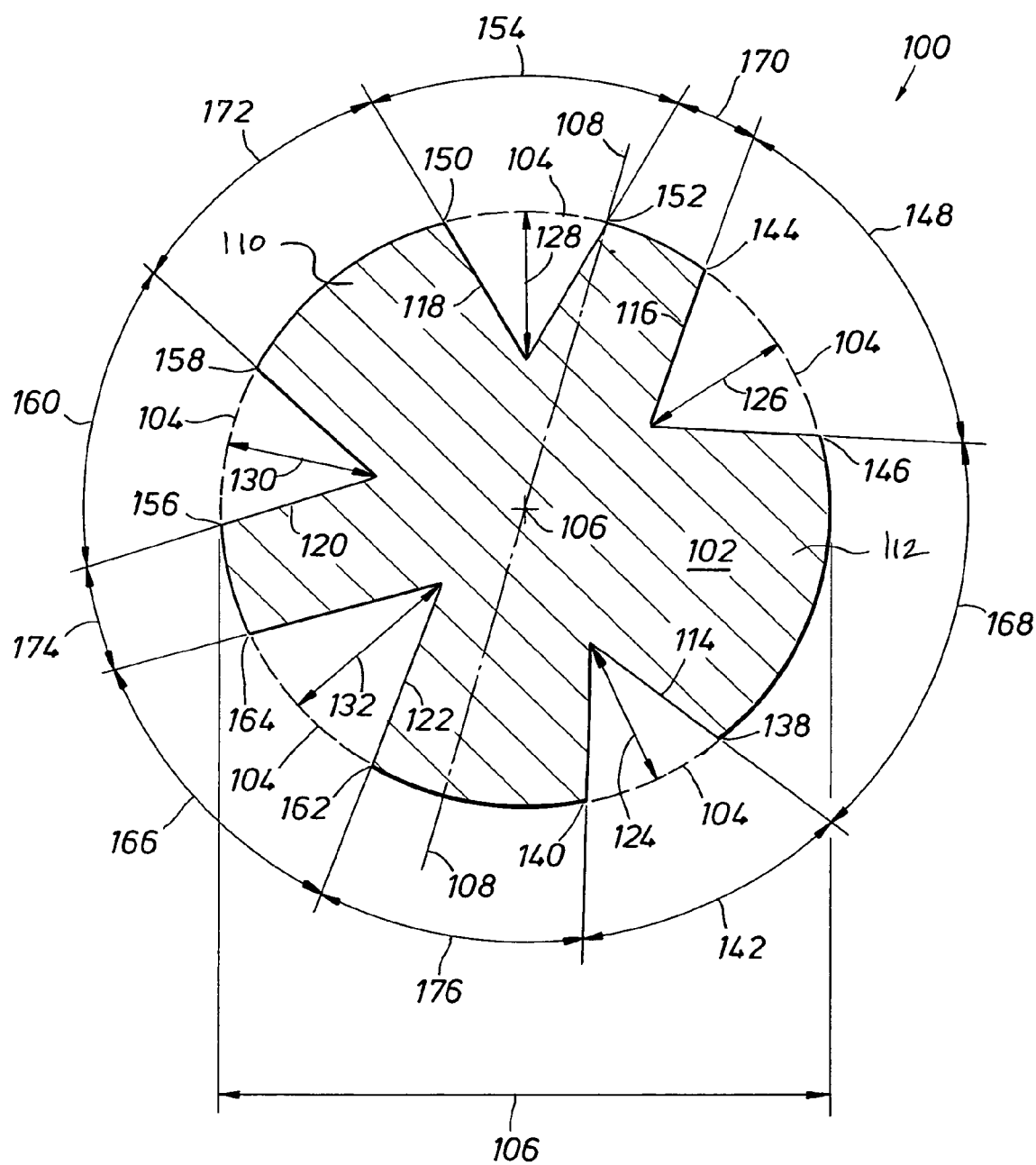
FIG. 3 is a cross sectional view of a five-grooved embodiment of the inventive shaped particle.

A cross section of another embodiment of the invention is presented in FIG. 3, which shows a cross sectional view of a five-grooved asymmetrical shape 100. The five-groove asymmetrical shape 100 has a cross sectional geometry 102 defined in part by an imaginary perimeter 104, which can have any suitable configuration or shape, but as shown in FIG. 3, the imaginary perimeter 104 approximates a circle having an axis 106.

The imaginary perimeter 104 is further defined as having a diameter 106 and an imaginary dividing line 108 passing through the axis 106. The imaginary dividing line 108 provides for or otherwise divides the cross sectional geometry 102 into an upper end or half 110 and a lower end or half 112.

The cross sectional geometry 102 defines a plurality of grooves including first groove 114, second groove 116, third groove 118, fourth groove 120 and fifth groove 122. First groove 114, second groove 116, third groove 118, fourth groove 120, and fifth groove 122 are respectively defined by a first groove depth 124, second groove depth 126, third groove depth 128, fourth groove depth 130, and fifth groove depth 132. The groove depth is the shortest distance of a line from a point on the imaginary perimeter 104 to the deepest point of the edge of the groove as measured from the imaginary perimeter 104, wherein the line is perpendicular to the tangent line passing through the point on the imaginary perimeter 104.

The opening of each groove of the plurality of grooves that is defined by the cross sectional geometry 102 can be characterized with reference to the number of degrees of the 360 rotational degrees that defines a circle. Thus, the first groove 114 includes a first leading edge 138 and a first trailing edge 140 that are spaced apart by a first groove opening rotational distance 142, which as previously noted may be measured in terms of degrees. The second groove 116 includes a second leading edge 144 and a second trailing edge 146 that are spaced apart by a second groove opening rotational distance 148. The third groove 118 includes a third leading edge 150 and a third trailing edge 152 that are spaced apart by a third groove opening rotational distance 154. The fourth groove 120 includes a fourth leading edge 156 and a fourth trailing edge 158 that are spaced apart by a fourth groove opening rotational distance 160. The fifth groove 118 includes a fifth leading edge 162 and a fifth trailing edge 164 that are spaced apart by a fifth groove opening rotational distance 166.

The outer edge of the cross sectional geometry 102 between each of the grooves of the plurality of grooves can be characterized with reference to the number of degrees of the 360 rotational degrees that defines a circle. Thus, the first leading edge 138 of the first groove 114 and the second trailing edge 146 of second groove 116 are spaced apart by a first rotational distance 168. The second leading edge 144 of the second groove 116 and the third trailing edge 152 of the third groove 118 are spaced apart by a second rotational distance 170. The third leading edge 150 of the third groove 118 and the fourth trailing edge 168 of the fourth groove 120 are spaced apart by a third rotational distance 172. The fourth leading edge 156 of the fourth groove 120 and the fifth trailing edge 164 of the fifth groove 122 are spaced apart by a fourth rotational distance 174. The fifth leading edge 162 of the fifth groove 122 and the first trailing edge 140 of the first groove 114 are spaced apart by a fifth rotational distance 176.

In moving along the imaginary perimeter 104 in a counter-clockwise direction, the trailing edge of a groove, for example the first trailing edge 140 of the first groove 114, is first encountered followed by the encountering of the first leading edge of the same groove, for example the leading edge 138 of the first groove 114. Next, the second trailing edge 146 of second groove 116 is encountered followed by the encountering of the second leading edge 144 of the second groove 116. Next, the third trailing edge 152 of the third groove 118 is encountered followed by the encountering of the third leading edge 150 of the third groove 118. Next, the fourth trailing edge 168 of the fourth groove 120 is encountered followed by the encountering of the fourth leading edge 156 of the fourth groove 120. Next, the fifth trailing edge 164 of the fifth groove 122 is encountered followed by the encountering of the fifth leading edge 162 of the fifth groove 122 and, then, back to the beginning at the first trailing edge 140.

The imaginary perimeter 104 starting at a point such as the first trailing edge of the first groove 114 and ending at the same spot represents 360 degrees. Thus, the summation of the first groove opening rotational distance 142, the second groove opening rotational distance 148, the third groove opening rotational distance 154, the fourth groove opening rotational distance 160, the fifth groove opening rotational distance 166, the first rotational distance 168, the second rotational distance 170, the third rotational distance 172, the fourth rotational distance 174, and the fifth rotational distance 176 is 360 degrees.

It should be understood that the three-grooved shape and five-grooved shape described above in respect to the figures are provided only as illustrative examples of certain of the embodiments of the invention. It is therefore understood that the inventive multi-grooved shape can also include shapes having four grooves or six or more grooves, provided, that the shapes meet the requirement of asymmetry and other geometric properties as are described herein. The spacing of the grooves, groove depths, groove opening rotational distances and rotational distances may vary significantly and are not necessarily limited to the relative dimensions and geometries that are depicted in the figures of this specification.

The inventive shaped particle may be prepared by any suitable method or means known to those skilled in the art by using any material that may suitably be formed into a shaped particle as defined herein. Suitable materials that may be used in the formation of the shaped particle include, for example, materials or compounds or components that are typically used in the formation of catalyst systems or compositions or that, in combination with other components, form catalyst systems or compositions. Methods of forming the shaped particle may include, for example, extrusion methods, molding methods and pill formation or tableting methods.

When the shaped particle is used in the formation or preparation of a catalyst system, it may be formed from typical catalyst support materials such as the porous inorganic oxides, which can include any refractory oxide material that has properties suitable for use as the support component of a catalyst system or composition. Examples of possible suitable porous refractory oxide materials include silica, magnesia, silica-titania, zirconia, silica-zirconia, titania, silica-titania, alumina, silica-alumina, and aluminosilicate. The alumina can be of various forms, such as, alpha alumina, beta alumina, gamma alumina, delta alumina, eta alumina, theta alumina, boehmite, or mixtures thereof.

When the shaped particle comprises a support material, catalytic components may further be introduced into the shaped particle by any of the known methods for incorporating catalytic components into a shaped catalyst support material, such as by standard impregnation methods. Also, the catalytic components may be co-mixed or co-mulled with the support material prior to the formation of the shaped particle to provide the shaped catalyst particle.

An especially important embodiment of the invention is an iron oxide-based dehydrogenation catalyst system that is in the form of the shaped particle as described herein. This is because dehydrogenation reactions, particularly the dehydrogenation of ethylbenzene to styrene, can be sensitive to reactor flow and pressure conditions, and the inventive shaped iron oxide-based catalyst system can provide for a reduced pressure drop across a bed of the shaped catalyst system as compared to other prior art shapes, and it can provide for improved flow characteristics through the bed.

The inventive shaped iron oxide-based catalyst system comprises iron oxide. The iron oxide of the dehydrogenation catalyst may be in any form and obtained from any source or by any method that provides a suitable iron oxide material for use in the iron oxide based dehydrogenation catalyst. One particularly desirable iron oxide based dehydrogenation catalyst includes potassium oxide and iron oxide.

The iron oxide of the iron oxide based dehydrogenation catalyst may be in a variety of forms including any one or more of the iron oxides, such as, for example, yellow iron oxide (goethite, FeOOH), black iron oxide (magnetite, $Fe_3O_4$), and red iron oxide (hematite, $Fe_2O_3$), including synthetic hematite or regenerated iron oxide, or it may be combined with potassium oxide to form potassium ferrite ($K_2Fe_2O_4$), or it may be combined with potassium oxide to form one or more of the phases containing both iron and potassium as represented by the formula $(K_2O)_x \cdot (Fe_2O_3)_y$.

Typical iron oxide based dehydrogenation catalysts comprise from 10 to 100 weight percent iron, calculated as $Fe_2O_3$, and up to 40 weight percent potassium, calculated as $K_2O$. The iron oxide based dehydrogenation catalyst may further comprise one or more promoter metals that are usually in the form of an oxide. These promoter metals may be selected from the group consisting of Sc, Y, La, Mo, W, Cs, Rb, Ca, Mg, V, Cr, Co, Ni, Mn, Cu, Zn, Cd, Al, Sn, Bi, rare earths and mixtures of any two or more thereof. Among the promoter metals, preferred are those selected from the group consisting of Ca, Mg, Mo, W, Ce, La, Cu, Cr, V and mixtures of two or more thereof. Most preferred are Ca, Mg, W, Mo, and Ce.

Descriptions of typical suitable iron oxide-based dehydrogenation catalyst compositions are found in patent publications that include U.S. Patent Publication No. 2003/0144566 A1; U.S. Pat. No. 5,689,023; U.S. Pat. No. 5,376,613; U.S. Pat. No. 4,804,799; U.S. Pat. No. 4,758,543; U.S. Pat. No. 6,551,958 B1; and EP 0,794,004 B1, all of such patent publications are incorporated herein by reference.

The shaped iron oxide based dehydrogenation catalyst, which comprises iron oxide and, preferably, further comprises potassium oxide, in general, can be prepared by combining the components of an iron-containing compound and a potassium-containing compound and shaping these components to form shaped particles followed by the calcination of the shaped particles. The promoter metal-containing compounds may also be combined with the iron-containing and potassium-containing components. The shaped iron oxide based dehydrogenation catalyst can comprise from 10 to 90 weight percent iron oxide, calculated as $Fe_2O_3$ and based on the total weight of the shaped iron oxide based catalyst. The shaped iron oxide based dehydrogenation catalyst can further comprise from 5 to 40 weight percent potassium oxide, calculated as $K_2O$ and based on the total weight of the shaped iron oxide based catalyst. The preferred concentration of iron oxide in the shaped iron oxide based dehydrogenation catalyst is in the range of from 20 to 85 weight percent, and most preferred, from 30 to 80 weight percent. The preferred concentration of potassium oxide in the shaped iron oxide based catalyst is in the range of from 10 to 35 weight percent, and most preferred, from 15 to 30 weight percent.

The catalyst components can be formed into the shaped particle as described herein by any suitable method. One preferred method of making the iron oxide-based dehydrogenation catalyst is to mix together the catalyst components with water or a plasticizer, or both, and forming an extrudable paste from which extrudates having the desired geometry are formed. The extrudates are then dried and calcined. The calcination is preferably done in an oxidizing atmosphere, such as air, and at temperatures upwardly to 1200° C., but preferably from 500° C. to 1100° C., and, most preferably, from 700° C. to 1050° C.

In order to provide the desired particle geometry and the required weight loading of the multi-grooved shaped particle or catalyst, the shaped particle should have at least three grooves, and it can have upwardly to as many as seven or eight grooves or even more grooves depending upon the size of the shaped particle and the amount of weight loading required for providing the desired function. Thus, in broad terms, the shaped particle of the invention can have from 3 to about 10 grooves, with each groove characterized as having a ratio of groove depth-to-diameter in the range of from about 0.075:1 to about 0.6:1, a groove opening rotational distance ($\theta$) in the range of from about 5 to about 70 degrees, a rotational distance ($\omega$) in the range of from about 20 to about 115 degrees, and a ratio of length-to-diameter in the range of from about 0.5 to about 2. In absolute terms, the nominal diameter of the shaped particle can be in the range of from 2 or 3 millimeters (mm) to 15 or 20 mm. Preferably, the nominal diameter of the shaped particle is in the range of from 3 mm to 10 mm, and, most preferably, the nominal diameter is in the range of from 3 mm to 8 mm.

To provide for the desired weight loading, it can also be desirable for the cross section of the shaped particle to have a geometry wherein the ratio of the cross sectional area of the upper end or half of the shaped particle to the cross sectional area of the lower end or half of the shaped particle is in the range of from 1.1:1 to 4:1. The terms "upper end" and "lower end" are defined in the above description in respect to the FIGs. It is preferred for the ratio of the cross sectional area of the upper end or half of the shaped particle to the cross sectional area of the lower end or half of the shaped particle to be in the range of from 1.25:1 to 3:1, and, most preferred, the ratio is in the range of from 1.5:1 to 2.5:1.

It is understood herein that in the manufacture of the shaped particles there are normal variations in the manufactured end-product dimensions and that the dimensions of the manufactured inventive shaped particles will vary within normal manufacturing tolerances. The variations will be more pronounced depending upon the method by which the shaped particle is manufactured. For instance, particles made by extrusion methods tend to have less uniformity than particles made by pilling methods. And, while the cross section of the inventive shape has been described with reference to an imaginary circular perimeter about an axis, it should be understood that the cross sectional shape may deviate from a circle and even include elongated cross sections, provided, that, the cross section is asymmetrical and includes the other required characteristics of the herein described invention. Also, the grooves as depicted in the figures hereof reflect a "V" shaped notch formed by two straight edges intersecting at a point to form a well-defined angle. While this geometry is one preferred embodiment, it is understood that, generally, the grooves may not be as well defined and that they may deviate somewhat from the depicted "V" shaped notches.

For the three grooved embodiment of the shaped particle, the groove depth-to-diameter ratio can be in the range of from 0.075:1 to 0.5:1, preferably, from 0.125:1 to 0.4:1, and, most preferably, from 0.15:1 to 0.375:1. The groove opening rotational distance can be in the range of from 10° to 60°, preferably, from 15° to 50°, and, most preferably, from 20° to 40°. The rotational distance can be in the range of from 60° to 110°, preferably, from 70° to 105°, and, most preferably, from 80° to 100°. The length-to-diameter ratio of the three-grooved shaped particle can be in the range of from about 0.5 to about 3.5, preferably, from 0.7 to 3.2, and, most preferably, from 1 to 3. It is common to target for a length-to-diameter ratio of close to 2, but the result may vary significantly depending upon the manufacturing method and conditions used to make the shaped particle.

For the five grooved embodiment of the shaped particle, the groove depth-to-diameter ratio can be in the range of from 0.075:1 to 0.5:1, preferably, from 0.125:1 to 0.4:1, and, most preferably, from 0.15:1 to 0.375:1. The groove opening rotational distance can be in the range of from 10° to 50°, preferably, from 15° to 40°, and, most preferably, from 20° to 35°. The rotational distance can be in the range of from 29.5° to 70°, preferably, from 35° to 65°, and, most preferably, from 40° to 60°. The length-to-diameter ratio of the five-grooved shaped particle can be in the range of from about 0.5 to about 3.5, preferably, from 0.7 to 3.2, and, most preferably, from 1 to 3. It is common to target for a length-to-diameter ratio of close to 2, but the result may vary significantly depending upon the manufacturing method and conditions used to make the shaped particle.

The following Table 1 presents in tabular form various of the dimensions of the inventive 3, 5 and 7 grooved shaped particle.

TABLE 1

Representative Broad, Intermediate, and Narrow Ranges for the Geometric Dimensions of the Multi-Grooved Asymmetrically Shaped Particle.

| Number of Grooves | Ratio of Groove Depth to Diameter | Groove Opening Rotational Distance (θ) | Rotational Distance (ω) | Ratio of Length to Diameter | Ratio of Upper End Cross Sectional Area to Lower End Cross Sectional Area |
|---|---|---|---|---|---|
| 3 | 0.1 to 0.5 | 10° to 60° | 60° to 110° | 0.5 to 3.5 | 1.1:1 to 4:1 |
|   | 0.125 to 0.4 | 15° to 50° | 70° to 105° | 0.7 to 3.2 | 1.25:1 to 3:1 |
|   | 0.15 to 0.375 | 20° to 40° | 80° to 100° | 1 to 3 | 1.5:1 to 2.5:1 |
| 5 | 0.075 to 0.5 | 10° to 50° | 29.5° to 70° | 0.5 to 3.5 | 1.1:1 to 4:1 |
|   | 0.125 to 0.4 | 15° to 40° | 35° to 65° | 0.7 to 3.2 | 1.25:1 to 3:1 |
|   | 0.15 to 0.375 | 20° to 35° | 40° to 60° | 1 to 3 | 1.5:1 to 2.5:1 |
| 7 | 0.1 to 0.5 | 5° to 30° | 20° to 50° | 0.5 to 3.5 | 1.1:1 to 4:1 |
|   | 0.125 to 0.4 | 10° to 25° | 25° to 40° | 0.7 to 3.2 | 1.25:1 to 3:1 |
|   | 0.15 to 0.375 | 15° to 20° | 30° to 35° | 1 to 3 | 1.5:1 to 2.5:1 |

As noted above, the preferred use of the inventive shaped particle is as an iron oxide-based dehydrogenation catalyst system. The shaped iron oxide based catalyst particle is placed or loaded into a reactor vessel so as to form a so-called packed bed of the shaped catalyst particles with the packed bed having a depth within the reactor vessel. The reactor vessel is equipped with a reactor feed inlet for receiving a dehydrogenation feedstock and a reactor effluent outlet for withdrawing a dehydrogenation reaction product. A dehydrogenation feed is passed through the catalyst bed to thereby contact the dehydrogenation feed with the shaped iron oxide-based dehydrogenation catalyst particles contained within the catalyst bed. This contacting of the dehydrogenation feed with the shaped iron oxide-based dehydrogenation is conducted under suitable dehydrogenation reaction conditions.

The dehydrogenation feed can be any suitable feed and, more particularly, it can include any hydrocarbon that is dehydrogenatable. Examples of dehydrogenatable hydrocarbons include substituted benzene compounds, such as ethylbenzene, isoamylenes, which can be dehydrogenated to isoprenes, and butenes, which can be dehydrogenated to butadiene. The preferred dehydrogenation feed comprises ethylbenzene, which can be dehydrogenated to styrene. The dehydrogenation feed can also include other components including diluents.

The dehydrogenation conditions can include a dehydrogenation reactor inlet temperature in the range of from about 500° C. to about 1000° C., preferably, from 525° C. to 750° C., and, most preferably, from 550° C. to 700° C. Thus, the first temperature of the dehydrogenation catalyst bed can range from about 500° C. to about 1000° C., more specifically, from 525° C. to 756° C., and, most specifically, from 550° C. to 700° C.

It is recognized, however, that in the dehydrogenation of ethylbenzene to styrene, the reaction is endothermic. When such a dehydrogenation reaction is carried out, it can be done so either isothermally or adiabatically. In the case where the dehydrogenation reaction is carried out adiabatically, the temperature across the dehydrogenation catalyst bed, between the dehydrogenation reactor inlet and the dehydrogenation reactor outlet, can decrease by as much as 150° C., but, more typically, the temperature can decrease from 10° C. to 120° C.

The reaction pressure is relatively low and can range from vacuum pressure upwardly to about 25 psia. In conducting the ethylbenzene dehydrogenation reaction, it is best to conduct the reaction under as low of pressure conditions as are possible, for instance from 5 psia to 20 psia. In this case, the use of the inventive shaped catalyst particle can be particularly beneficial by providing for a desired low-pressure reaction condition.

The liquid hourly space velocity (LHSV) can be in the range of from about 0.01 hr$^{-1}$ to about 10 hr$^{-1}$, and preferably, from 0.1 hr$^{-1}$ to 2 hr$^{-1}$. As used herein, the term "liquid hourly space velocity" is defined as the liquid volumetric flow rate of the dehydrogenation feed, for example, ethylbenzene, measured at normal conditions (i.e., 0° C. and 1 bar absolute), divided by the volume of the catalyst bed, or the total volume of catalyst beds if there are two or more catalyst beds. When styrene is being manufactured by the dehydrogenation of ethylbenzene, it is generally desirable to use steam as a diluent usually in a molar ratio of steam to ethylbenzene in the range of 0.1 to 20. Steam may also be used as a diluent with other dehydrogenatable hydrocarbons.

It is understood that while particular embodiments of the invention have been described herein, reasonable variations, modifications and adaptations thereof may be made within the scope of the described disclosure and the appended claims without departing from the scope of the invention as defined by the claims.

That which is claimed is:

1. A shaped particle having a geometry including a length and a cross sectional geometry at at least one point along said length, wherein said cross sectional geometry is defined by an asymmetrical shape having an imaginary dividing line providing for an upper end, having an upper end cross sectional area, and a lower end, having a lower end cross sectional area, wherein said upper end cross sectional area is greater than said lower end cross sectional area, wherein said cross sectional geometry is further defined by a circle perimeter having a diameter and a center through which said imaginary dividing line passes;
   wherein said cross sectional geometry defines a plurality of grooves wherein each groove of said plurality of grooves is characterized by a groove depth, a leading edge and a trailing edge with said leading edge and said trailing edge spaced apart by a groove opening rotational distance;
   wherein said leading edge of each groove of said plurality of grooves is spaced apart from said trailing edge of an adjacent groove by a rotational distance; and wherein the summation of all of said groove opening rotational distances and all of said rotational distances of said cross sectional geometry is 360°.

2. A shaped particle as recited in claim 1, wherein said each groove of said plurality of grooves is defined by a ratio of groove depth-to-diameter in the range of from 0.075:1 to 0.6:1;
   wherein each said groove opening rotational distance is in the range of from 10° to 70° and
   wherein each said rotational distance is in the range of from 20° to 115°.

3. A shaped particle as recited in claim 2, wherein said groove depth of each groove of said plurality of grooves is defined as the linear distance of a line from a perimeter point on said circular perimeter to a depth point at the deepest point of the respective groove within said cross sectional geometry, wherein said line is perpendicular to the tangent line passing through said perimeter point on said circular perimeter.

4. A shaped particle as recited in claim 3, wherein said plurality of grooves includes:
   a first groove having a first groove depth, a first leading edge and a first trailing edge with said first leading edge and said first trailing edge spaced apart by a first groove opening rotational distance;
   a second groove having a second groove depth, a second leading edge and a second trailing edge with said second leading edge and said second trailing edge spaced apart by a second groove opening rotational distance;
   a third groove having a third groove depth, a third leading edge and a third trailing edge with said third leading edge and said third trailing edge spaced apart by a third groove opening rotational distance;
   wherein said first leading edge of said first groove is spaced apart from said second trailing edge of said second groove by a first rotational distance;
   wherein said second leading edge of said second groove is spaced apart from said third trailing edge of said third groove by a second rotational distance; and
   wherein said third leading edge of said third groove is spaced apart from said first trailing edge of said first groove by a third rotational distance.

5. A shaped particle as recited in claim 4,
   wherein the first groove has a ratio of first groove depth-to-diameter in the range of from 0.1:1 to 0.5:1; wherein said first groove opening rotational distance is in the range of from 10° to 60°;
   wherein said first rotational distance is in the range of from 60° to 110°;
   wherein the second groove has a ratio of second groove depth-to-diameter in the range of from 0.1:1 to 0.5:1;
   wherein said second groove opening rotational distance is in the range of from 10° to 60°; wherein said second rotational distance is in the range of from 60° to 110°;
   wherein the third groove has a ratio of third groove depth-to-diameter in the range of from 0.1:1 to 0.5:1;
   wherein said third groove opening rotational distance is in the range of from 10° to 60°;
   and wherein said third rotational distance is in the range of from 60° to 110°.

6. A shaped particle as recited in claim 3, wherein said plurality of grooves includes:

a first groove having a first groove depth, a first leading edge and a first trailing edge with said first leading edge and said first trailing edge spaced apart by a first groove opening rotational distance;

a second groove having a second groove depth, a second leading edge and a second trailing edge with said second leading edge and said second trailing edge spaced apart by a second groove opening rotational distance;

a third groove having a third groove depth, a third leading edge and a third trailing edge with said third leading edge and said third trailing edge spaced apart by a third groove opening rotational distance;

a fourth groove having a fourth groove depth, a fourth leading edge and a fourth trailing edge with said fourth leading edge and said fourth trailing edge spaced apart by a fourth groove opening rotational distance;

a fifth groove having a fifth groove depth, a fifth leading edge and a fifth trailing edge with said fifth leading edge and said fifth trailing edge spaced apart by a fifth groove opening rotational distance;

wherein said first leading edge of said first groove is spaced apart from said second trailing edge of said second groove by a first rotational distance;

wherein said second leading edge of said second groove is spaced apart from said third trailing edge of said third groove by a second rotational distance; and wherein said third leading edge of said third groove is spaced apart from said fourth trailing edge of said fourth groove by a third rotational distance;

wherein said fourth leading edge of said fourth groove is spaced apart from said fifth trailing edge of said fifth groove by a fourth rotational distance; and wherein said fifth leading edge of said fifth groove is spaced apart from said first trailing edge of said first groove by a fifth rotational distance.

7. A shaped particle as recited in claim 6,
wherein the first groove has a ratio of first groove depth-to-diameter in the range of from 0.075:1 to 0.5:1; wherein said first groove opening rotational distance is in the range of from 10° to 50°;

wherein said first rotational distance is in the range of from 29.5° to 70°;

wherein the second groove has a ratio of second groove depth-to-diameter in the range of from 0.075:1 to 0.5:1; wherein said second groove opening rotational distance is in the range of from 10° to 50°; wherein said second rotational distance is in the range of from 29.5° to 70°;

wherein the third groove has a ratio of third groove depth-to-diameter in the range of from 0.075:1 to 0.5:1; wherein said third groove opening rotational distance is in the range of from 10° to 50°; and wherein said third rotational distance is in the range of from 29.5° to 70°;

wherein the fourth groove has a ratio of fourth groove depth-to-diameter in the range of from 0.075:1 to 0.5:1; wherein said fourth groove opening rotational distance is in the range of from 10° to 50°; wherein said fourth rotational distance is in the range of from 29.5° to 70°;

wherein the fifth groove has a ratio of fifth groove depth-to-diameter in the range of from 0.075:1 to 0.5:1; wherein said fifth groove opening rotational distance is in the range of from 10° to 50°;

and wherein said fifth rotational distance is in the range of from 29.5° to 70°.

* * * * *